(12) United States Patent
Green et al.

(10) Patent No.: US 9,772,304 B2
(45) Date of Patent: Sep. 26, 2017

(54) METHOD OF CHARGE STATE SELECTION (71) Applicant: Micromass UK Limited, Wilmslow (GB)

(72) Inventors: Martin Raymond Green, Bowdon (GB); Keith Richardson, Derbyshire (GB); Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 15/100,034

(22) PCT Filed: Dec. 1, 2014

(86) PCT No.: PCT/GB2014/053556
§ 371 (c)(1),
(2) Date: May 27, 2016

(87) PCT Pub. No.: WO2015/082889
PCT Pub. Date: Jun. 11, 2015

(65) Prior Publication Data
US 2017/0003250 A1    Jan. 5, 2017

(30) Foreign Application Priority Data

Dec. 2, 2013  (EP) .................................... 13195360
Dec. 2, 2013  (GB) .................................... 1321246.9

(51) Int. Cl.
*G01N 27/447* (2006.01)
*H01J 49/04* (2006.01)
(Continued)

(52) U.S. Cl.
CPC ... *G01N 27/44717* (2013.01); *G01N 27/4473* (2013.01); *G01N 27/44782* (2013.01);
(Continued)

(58) Field of Classification Search
None
See application file for complete search history.

(56) References Cited

U.S. PATENT DOCUMENTS 6,958,473 B2   10/2005   Belov et al.
7,985,948 B2   7/2011    Bonner et al.
(Continued)

OTHER PUBLICATIONS

Williams et al., "Utility of CE—MS Data in Protein Identification", Anal. Chem., vol. 79, pp. 3850-3855, 2007.*
(Continued)

*Primary Examiner* — Jack Berman
(74) *Attorney, Agent, or Firm* — Diederiks & Whitelaw, PLC (57) ABSTRACT

A method of mass spectrometry or ion mobility spectrometry is disclosed in which analyte ions of a desired charge state are isolated. The method comprises: separating analytes according to their electrophoretic mobility; ionizing the analytes; and mass filtering the resulting analyte ions, wherein the mass to charge ratios of the ions transmitted by a mass filter are varied as a function of the electrophoretic mobility and according to a predetermined relationship such that substantially only ions having said desired charge state are transmitted by the mass filter.

10 Claims, 6 Drawing Sheets

(51) Int. Cl.
*H01J 49/00* (2006.01)
*G01N 27/62* (2006.01)

(52) U.S. Cl.
CPC ..... *G01N 27/44791* (2013.01); *G01N 27/624* (2013.01); *H01J 49/0027* (2013.01); *H01J 49/0031* (2013.01); *H01J 49/0404* (2013.01); *H01J 49/004* (2013.01)

(56) References Cited

U.S. PATENT DOCUMENTS

| | | | |
|---|---|---|---|
| 8,030,089 B2 * | 10/2011 | Geromanos | C12Q 1/6872 436/173 |
| 8,581,176 B2 | 11/2013 | Thomson et al. | |
| 9,040,903 B2 | 5/2015 | Coon et al. | |
| 9,410,927 B2 | 8/2016 | Bateman et al. | |
| 2015/0041636 A1 | 2/2015 | Giles et al. | |

OTHER PUBLICATIONS

"*Introduction to Mass Spectrometry, Chapter 3: Mass Spectrometry/Mass Spectrometry*", pp. 173-228, 2007.

* cited by examiner

METHOD OF CHARGE STATE SELECTION

CROSS REFERENCE TO RELATED APPLICATIONS

This application is the National Stage of International Application No. PCT/GB2014/053556, filed 1 Dec. 2014 which claims priority from and the benefit of United Kingdom patent application No. 1321246.9 filed on 2 Dec. 2013 and European patent application No. 13195360.6 filed on 2 Dec. 2013. The entire contents of these applications are incorporated herein by reference.

BACKGROUND TO THE PRESENT INVENTION

The preferred embodiments of the present invention relate to the use of capillary electrophoresis to separate analytes.

Capillary electrophoresis ("CE") is a known technique which is used to separate ionic species in a conductive medium in the presence of an electric field. Capillary electrophoresis causes ions in solution to migrate with velocities based on their solution charge (i.e. charge when in solution), hydrodynamic radius and frictional forces.

The preferred embodiments of the present application relate to new uses of capillary electrophoresis to provide improved methods of mass spectrometry or ion mobility spectrometry and improved mass spectrometers or ion mobility spectrometers.

SUMMARY OF THE PRESENT INVENTION

From a first aspect the present invention provides a method of mass spectrometry or ion mobility spectrometry comprising:

separating analytes in a separator such that analytes having different electrophoretic mobilities elute from the separator at different times;

ionising the separated analytes as they elute from the separator so as to form analyte ions that are separated from each other;

transmitting the separated analyte ions to a mass filter;

obtaining a predetermined relationship between the elution times of the analytes from the separator, the mass to charge ratios of the analyte ions, and the charge states of the analyte ions;

selecting one or more charge states of the analyte ions desired to be transmitted by the mass filter; and varying the mass to charge ratios of the ions transmitted by the mass filter as a function of the elution time of the analytes from the separator and according to said predetermined relationship such that substantially only ions having said one or more desired charge states are transmitted by the mass filter.

The present invention recognises that the electrophoretic mobility of an analyte in solution is correlated to the gas-phase charge state and mass to charge ratio of the analyte when ionised. This relationship may therefore be used to select the charge state of ions.

It is known to separate analytes, to ionise the separated analytes, and to then mass filter the resulting ions. For example, WO 2010/135829 discloses a tandem mass spectrometer in which one of the mass filters is scanned with time. Analytes are separated according to their molecular weight upstream of the mass filter so that different analytes are delivered to the mass filter at different times, allowing the mass filter to selectively transmit a desired analyte at any given time without wasting other analytes, which are delayed by the molecular weight separator. As the mass filter transmits ions, rather than the molecules transmitted from the molecular weight separator, the filter must account for the charge state of the ions when selecting the mass to charge ratios of the ions to be transmitted by the mass filter. The technique therefore sets the mass filter to transmit ions having a fraction of the molecular weight eluting from the separator. For example, when a molecular weight of 600 is eluting the filter is stepped between 600 for singly charged ions, 300 for doubly charged ions and 200 for triply charged ions, such that if singly, doubly or triply charged analyte ions are present then these will be transmitted.

However, WO 2010/135829 does not recognise that the charge states of the analyte ions follow a trend as a function of electrophoretic mobility and mass to charge ratio, and that this trend can be used to select analyte ions of desired charge states. Rather, WO 2010/135829 simply steps between different filter settings for each molecular weight that is eluting so as to ensure that if various different charge states are present then ions will be transmitted for each of these charge states. Accordingly, there is no motivation from this teaching to use a predetermined relationship between charge state, electrophoretic mobility and mass to charge ratio in order to isolate ions of desired charge state.

Other systems are know that separate analytes by electrophoretic mobility and which then filter the ions, such as that of US 2005/0211891. However, this technique also does not recognise that the charge states of the analyte ions follow a trend as a function of electrophoretic mobility and mass to charge ratio, and that this trend can be used to select analyte ions of desired charge states.

Said step of varying the mass to charge ratios of the ions transmitted by the mass filter preferably filters out substantially all ions other than ions having said one or more desired charge states. Ions of other charge states are therefore filtered out.

The method preferably does not transmit all of the charge states present for any given analyte ion, but only transmits one or some of the charge states present for the analyte ion.

Preferably, said predetermined relationship is known or determined in advance of said step of varying the mass to charge ratios of the ions transmitted by the mass filter.

For analyte ions in each of said one or more desired charge states in said predetermined relationship, the mass to charge ratios preferably progressively increase without decreasing, or progressively decrease without increasing, as a function of increasing electrophoretic mobility. Alternatively, or additionally, the mass to charge ratio or range of mass to charge ratios transmitted by the mass filter at any given time preferably progressively increases without decreasing, or progressively decreases without increasing, as a function of increasing electrophoretic mobility such that said one or more desired charge states are transmitted by the mass filter.

The mass to charge ratio or range of mass to charge ratios transmitted by the mass filter may continuously increase or continually decrease, or increase or decrease in a stepped manner.

Preferably, the analyte ions in each of said one or more desired charge states in said predetermined relationship follow a trend of mass to charge ratio as a function of electrophoretic mobility, and the filter is varied so as to transmit analyte ions that follow said trend.

The method may comprise simply looking up the predetermined relationship. Alternatively, the method may comprise experimentally determining the relationship in advance of performing the above-described method. The method may therefore comprise determining the charge states of the analyte ions as a function of the mass to charge ratios of the analyte ions and as a function of the elution times from the separator of the respective analytes, in order to identify said relationship.

The method preferably comprises separating the analytes so that they elute from the separator over a period of time and varying the mass to charge ratios of the ions transmitted by the filter in synchronism with said period of time.

The filter may operate as a band pass filter so as to transmit ions having a range of mass to charge ratios within upper and lower limits at any given time, and said range of mass to charge ratios that is transmitted may be varied as a function of the elution time of the analytes from the separator. Alternatively, the filter may operate as a high pass filter so as to transmit ions having mass to charge ratios above a cut-off value at any given time, and the cut-off value may be varied as a function of the elution time of the analytes from the separator. Alternatively, the filter may operate as a low pass filter so as to transmit ions having mass to charge ratios below a cut-off value at any given time, and the cut-off value may be varied as a function of the elution time of the analytes from the separator.

The may comprise transmitting the analyte ions of said one or more desired charge states from said filter to a fragmentation or reaction region; fragmenting the analyte ions to form fragment ions, or reacting the analyte ions with other ions or molecules to form product ions; and mass analysing or ion mobility analysing the fragment or product ions. Filtering the ions prior to fragmentation or reaction provides the advantage that the likelihood of the fragment ion intensity or mass to charge ratio information being corrupted due to mass interference is reduced.

The separator may separate the analytes by Capillary Electrochromatography ("CEC") or Micellar Electrokinetic Chromatography ("MEKC").

Although there is a weaker correlation between mass to charge ratio, charge state and retention time for other liquid chromatography techniques, some correlation does exist. Accordingly, the present invention is not limited to electrophoretic mobility separators.

Also, although a mass filter has been described, a filter for filtering ions according to another physicochemical property may be used instead.

Accordingly, from a second aspect the present invention provides a method of mass spectrometry or ion mobility spectrometry comprising:

separating analytes in an electrophoretic mobility separator or a liquid chromatography separator such that different analytes elute from the separator at different times;

ionising the separated analytes after they elute from the separator so as to form analyte ions that are separated from each other;

transmitting the separated analyte ions to a filter for filtering ions according to a physicochemical property;

obtaining a predetermined relationship between the elution times of the analytes from the separator, the physicochemical property values of the analyte ions, and the charge states of the analyte ions;

selecting one or more charge states of the analyte ions desired to be transmitted by the filter; and varying the physicochemical property values of the ions transmitted by the filter as a function of the elution time of the analytes from the separator and according to said predetermined relationship such that substantially only ions having said one or more desired charge states are transmitted by the mass filter.

The step of separating analytes may comprise separating analytes such that analytes having different electrophoretic mobilities elute from the separator at different times. However, the physicochemical property is preferably a property other than, but preferably correlated with, electrophoretic mobility.

The liquid chromatography may separate the analytes based on their charge in solution or based on their masses.

The liquid chromatography may be Size Exclusion Chromatography ("SEC"), Ion Exchange Chromatography ("IEX") or pH gradient chromatography.

The filter may be an ion mobility filter and the physicochemical property may be the gas phase ion mobility of the analyte ions through an ion mobility separator. Alternatively, the filter may be a differential ion mobility filter and the physicochemical property may be the differential ion mobility of the analyte ions. Alternatively, the filter may be a Field Asymmetric Ion Mobility Spectrometry (FAIMS) filter and the physicochemical property may be field asymmetric ion mobility of the analyte ions. For example, in a FAIMS device ions travel through the device along a longitudinal axis. The ions are subjected to an asymmetric AC voltage that are urges the ions, on average, in a first direction that is orthogonal to the longitudinal axis. Ions are urged in the opposite direction by a DC compensation voltage. It has been discovered that the value of the compensation voltage in a FAIMS device has a strong charge-state dependence and so the correlation can be used to give optimum transmission characteristics for a particular charge state if the relationship is predetermined.

The physicochemical property may be ion mobility in a Field Asymmetric Ion Mobility Spectrometer (FAIMS) device.

The second aspect of the present invention may have any one or combination of the preferred or optional features described in relation to the first aspect of the present invention, except wherein when the mass to charge ratio and mass filter are referred to in relation to the first aspect, these correspond to the physicochemical property and the filter for filtering ions according to the physicochemical property in the second aspect.

For example, the step of varying the physicochemical property values of the ions transmitted by the filter preferably filters out substantially all ions other than ions having said one or more desired charge states.

Said predetermined relationship is known or determined in advance of said step of varying the physicochemical property values of the ions transmitted by the filter.

Preferably, for analyte ions in each of said one or more desired charge states in said predetermined relationship, the physicochemical property values progressively increase without decreasing, or progressively decrease without increasing, as a function of increasing elution time from the separator.

Alternatively, or additionally, the physicochemical property values or range of physicochemical property values transmitted by the filter may progressively increase without decreasing, or progressively decrease without increasing, as a function of increasing elution time from the separator such that said desired charge states are transmitted by the filter.

Preferably, the physicochemical property value or range of physicochemical property values transmitted by the filter continuously increases or continually decreases, or increases or decreases in a stepped manner.

Preferably, the analyte ions in each of said one or more desired charge states in said predetermined relationship follow a trend of said physicochemical property as a function of elution times from the separator, and wherein the filter is varied so as to transmit analyte ions that follow said trend.

The method may comprise simply looking up the predetermined relationship. Alternatively, the method may comprise determining the relationship in advance of performing the above-described method. The method may therefore comprise determining the charge states of the analyte ions as a function of the physicochemical property of the analyte ions and as a function of the elution times from the separator of the respective analytes, in order to identify said relationship.

The method may comprise separating the analytes so that they elute from the separator over a period of time and varying the physicochemical property values of the ions transmitted by the filter in synchronism with said period of time.

The filter may operate as a band pass filter so as to transmit ions having a range of physicochemical property values within upper and lower limits at any given time, and said range of physicochemical property values that is transmitted may be varied as a function of the elution time of the analytes from the separator. Alternatively, the filter may operate as a high pass filter so as to transmit ions having physicochemical property values above a cut-off value at any given time, and the cut-off value may be varied as a function of the elution time of the analytes from the separator. Alternatively, the filter may operate as a low pass filter so as to transmit ions having physicochemical property values below a cut-off value at any given time, and the cut-off value may be varied as a function of the elution time of the analytes from the separator.

The method may comprise transmitting the analyte ions of said one or more desired charge states from said filter to a fragmentation or reaction region; fragmenting the analyte ions to form fragment ions, or reacting the analyte ions with other ions or molecules to form product ions; and mass analysing or ion mobility analysing the fragment or product ions.

The separator may separate the analytes by Capillary Electrochromatography ("CEC") or Micellar Electrokinetic Chromatography ("MEKC").

From a third aspect the present invention provides a method of mass spectrometry or ion mobility spectrometry comprising:

separating analytes in a separator such that analytes having different electrophoretic mobilities elute from the separator at different times;

ionising the separated analytes as they elute from the separator so as to form analyte ions that are separated from each other;

transmitting the analyte ions to at least one device that manipulates the ions; and varying the operation of the at least one device based on the elution time of the analytes from the separator.

The present invention recognises that the electrophoretic mobility of an analyte in solution may be correlated to the gas-phase charge state and mass to charge ratio of the analyte when ionised. This technique may therefore be used to provide analyte ions to a downstream device such that the different analyte ions are separated, without having to separate the ions in the gas phase. The operation of the device may then be varied depending on the elution time from the electrophoretic mobility separator, i.e. to operate differently for different analyte ions. This may be used to enhance or simplify the data recorded for the analyte ions.

The at least one device may comprise a gas phase ion mobility separator that accumulates the analyte ions and periodically releases them into an ion mobility separation region of the ion mobility separator as a packet of ions; and wherein the frequency and/or duty cycle at which the packets of ions are released into the ion mobility separator is varied as a function of elution time of the electrophoretic mobility separator.

Accordingly, the frequency and/or duty cycle at which ions are released into the ion mobility separator is different for ions of different electrophoretic mobility.

The method preferably comprises obtaining a predetermined relationship between the elution times of the analytes from the separator and the frequency and/or duty cycle at which the packets of ions are to be released into the ion mobility separator. The predetermined relationship preferably relates the optimum frequency and/or duty cycle for the ions to their elution times. The frequency and/or duty cycle at which the packets of ions are released into the ion mobility separator may then be varied as a function of elution time and according to the predetermined relationship.

The method preferably comprises experimentally determining the predetermined relationship.

For a given packet of ions that is released into the separation region of the ion mobility separator, one or more further packet of ions is preferably subsequently released into the separation region whilst at least some of the ions from said given packet of ions are still travelling through and/or being separated in the ion mobility separator.

The frequency and/or duty cycle may be varied such that no overlapping of ion species from different packets of ions occurs within the ion mobility separator.

This method may be advantageous for minimising space-charge effects such as peak broadening or drift time shifting in the gas phase ion mobility separator.

The at least one device may comprise a gas phase ion mobility separator, wherein one or more potential well or hill is periodically conveyed along the ion mobility separator so as to drive analyte ions through the device, and wherein the amplitude and/or velocity of the one or more potential well or hill is varied as a function of the elution time from the electrophoresis separator.

The potential well or hill is preferably a DC well or hill.

The amplitude and/or velocity of the one or more potential well may be varied with time as it travels along the device. Alternatively, the amplitude and/or velocity of at least a first potential well or hill may remain constant as it travels along the device and the amplitude and/or velocity of at least a subsequent second potential well or hill may be varied relative to the first potential well or hill.

By varying the potential wells or hills, ion mobility separation conditions such resolution or elution time may be optimised for analyte ions eluting from the capillary electrophoresis device.

The at least one device may comprise a fragmentation device that fragments the analyte ions and wherein a fragmentation condition in the fragmentation device is varied based on:

(i) the elution time from the electrophoretic mobility separator; or (ii) a combination of the elution time from the electrophoretic mobility separator and the mass to charge ratio of the analyte ions being fragmented; or (iii) the ratio of the elution time from the electrophoretic mobility separator to the mass to charge ratio of the analyte ions being fragmented.

Preferably, the fragmentation condition is varied based such that different ions are subjected to different fragmentation conditions.

The method preferably comprises obtaining a predetermined relationship between the elution times of the analytes from the separator and the optimum fragmentation conditions. The fragmentation conditions may then be varied as a function of elution time and according to the predetermined relationship.

The method preferably comprises experimentally determining the predetermined relationship.

Preferably, the fragmentation device fragments the analyte ions by collisionally induced dissociation (CID) and the collision energy with which the ions are fragmented is varied as a function of elution time from the electrophoretic mobility separator.

The fragmentation technique is preferably varied as a function of elution time from the electrophoretic mobility separator such that a first type of fragmentation technique is used to fragment analyte ions of analyte that elutes from the separator during a first time period and a second, different type of fragmentation technique is used to fragment analyte ions of analyte that elutes from the separator during a second time period.

The first and/or second technique may be selected from electron transfer dissociation (ETD); electron capture dissociation (ECD); and collisionally induced dissociation (CID).

Analytes having a relatively high charge state in solution (i.e. during electrophoretic mobility separation) tend to have a relatively high electrophoretic mobility, and may be ionised to provide relatively high charge state ions in the gas-phase. Analytes having a relatively low charge state in solution (i.e. during electrophoretic mobility separation) tend to have a relatively low electrophoretic mobility, and may be ionised to provide relatively low charge state ions in the gas-phase. It is preferred that analyte ions having a high charge state in the gas-phase are fragmented by ETD or ECD, whereas analyte ions having a lower charge state in the gas-phase are fragmented by CID. The analyte ions fragmented by ETD or ECD preferably have a charge state in the gas-phase of at least ±2 or at least ±3. Analyte ions fragmented by CID fragmentation may have a charge state in the gas-phase of ±1 or less preferably ±2.

Analyte ions generated from analytes that elute with an elution time representative of a relatively high electrophoretic mobility may be fragmented by electron transfer dissociation (ETD) or electron capture dissociation (ECD), whereas analyte ions generated from analytes that elute with an elution time representative of a lower electrophoretic mobility may be fragmented by collisionally induced dissociation (CID).

The fragmentation technique may be selected based on the elution time alone. However, some analyte ions of high electrophoretic mobility may not form high gas-phase charge states and so would not ideally be subjected to certain fragmentation techniques, such as ETD/ECD fragmentation. For example, singly charged, low mass analytes may have high mobilities but low gas-phase charge states when ionised, and so it would not be particularly desirable to fragment such ions by ETD or ECD.

The present invention may improve the method of selecting which fragmentation technique to use by estimating the gas-phase charge states of the analyte ions. The fragmentation technique may then be selected based on the estimated gas-phase charge states of the ions to be fragmented. More specifically, for analyte ions of a particular gas-phase charge state, the mass to charge ratios of the analyte ions tend to be well correlated to the electrophoretic mobilities of their respective analytes and follow a particular trend. It is therefore possible to estimate the gas-phase charge states of the analyte ions from their mass to charge ratios and the electrophoretic mobilities of their respective analytes in solution.

Accordingly, the method of the present invention may determine the mass to charge ratios of the analyte ions. Preferably, the method comprises transmitting the analyte ions to a mass analyser and determining the mass to charge ratios of the analyte ions as a function of the elution times of the respective analytes from the electrophoretic mobility separator. If the electrophoretic mobility elution time of an analyte is known and the mass to charge ratio of its gas-phase ion is known, then the gas-phase charge state of the analyte ion can be determined. The fragmentation technique can then be selected based on the determined gas-phase charge state.

Therefore, the method may comprise determining the mass to charge ratio of any given analyte ion, determining the electrophoretic mobility elution time of its respective analyte, selecting one of plural fragmentation techniques based on the determined mass to charge ratio and elution time, and fragmenting the ions according to the selected technique. The fragmentation technique may be selected based on the ratio of the mass to charge ratio of the analyte ion and the elution time of its respective analyte.

The method may comprise transmitting analyte ions to a mass filter and using the mass filter to mass selectively transmit analyte ions to a fragmentation device. The fragmentation technique may then be selected based on the mass to charge ratio of the ion transmitted and the elution time of its respective analyte. The different fragmentation techniques that may be selected may be performed in the same fragmentation device. Alternatively, the analyte ions may be directed into different fragmentation devices when different fragmentation techniques are desired.

The mass to charge ratios transmitted by the mass filter are preferably varied as a function of elution time. The mass to charge ratios transmitted are preferably varied with elution time such that substantially only analyte ions within a particular gas-phase charge state are transmitted. This may be achieved by the mass filter only transmitting a band of mass to charge ratios between an upper and lower limit at any given time, and varying the upper and lower limit with time. Two or more separate bands having different upper and lower limits may be transmitted simultaneously. Alternatively, only analyte ions having a gas-phase charge state above a particular value may be transmitted. This may be achieved by the mass filter only transmitting mass to charge ratios above a particular value at any given time, and varying said particular value with time. Alternatively, only analyte ions having a gas-phase charge state below a particular value may be transmitted. This may be achieved by the mass filter only transmitting mass to charge ratios below a particular value at any given time, and varying said particular value with time.

The method may comprise conducting a survey scan of the analyte ions in order to determine which ions should be selectively transmitted for fragmentation. The ion signal, mass to charge ratios and/or elution times may be measured during such a survey scan and used to determine which ions to fragment.

Preferably, the fragment ions are subjected to mass analysis and/or ion mobility analysis. The properties of the fragment ions are preferably used to identify their parent ions.

The at least one device may comprise a time of flight mass analyser having an ion trap that accumulates analyte ions and periodically releases packets of analyte ions into or towards an extraction region of the mass analyser, wherein the extraction region pulses each of said packets of ions into a time of flight region of the mass analyser, wherein there is a delay period between the time at which any given packet of ions is released into or towards the extraction region and the time at which the extraction region pulses that packet of ions into the time of flight region, and wherein the delay period is varied in duration as a function of the elution time from the electrophoretic mobility separator.

As the capillary electrophoresis separation proceeds, the mass to charge ratio range eluting preferably changes. By varying the time delay between the release of an ion pulse into or towards the extraction region and the energising of the acceleration pulse in the extraction region, the method enables the acceleration voltage pulse in the extraction region to be synchronised with the arrival of ions within the extraction region, even though the mass to charge ratios of the ions vary over time. As such, high sampling efficiency may be maintained over the entire mass to charge ratio range.

The at least one device may comprise a time of flight mass analyser having an ion trap that accumulates analyte ions and periodically releases packets of analyte ions into or towards an extraction region of the mass analyser, wherein the extraction region pulses each of said packets of ions into a time of flight region of the mass analyser, and wherein the frequency at which the packets of ions are released into or towards the extraction region is varied as a function of elution time of the electrophoretic mobility separator.

The Time of Flight mass analyser described herein is preferably an orthogonal time of flight mass analyser, although less preferably it may be a linear time of flight mass analyser.

The at least one device may be a mass selective ion trap that accumulates said analyte ions and ejects analyte ions having a defined range of mass to charge ratios at any given time, and wherein the range of mass to charge ratios ejected from the ion trap is varied as a function of the elution time from the electrophoretic mobility separator.

The mass range ejected from the ion trap may be scanned continuously or stepped with time. The mass range over which the analytical ion trap is scanned or stepped is preferably varied to accommodate the mass to charge ratio range eluting from the capillary electrophoresis device. As such, the speed of mass selective ejection (i.e. amu per unit time) may be minimised, thus maximising mass resolution of the instrument.

The method may further comprise detecting or mass analysing ions transmitted by the at least one device; detecting or mass analysing ions ejected from the at least one device; or using the at least one device to detect or mass analyse the analyte ions.

The methods described herein may comprise a number of general features. For example, the analyte ions may be mass analysed in a mass analyser so as to determine their mass to charge ratios.

The separator preferably separates different analytes in a mixture of analytes in solution.

The analytes are preferably separated by capillary electrophoresis.

The analytes may be peptides, although other types of analytes are also contemplated.

The ions are preferably ionised by an electrospray ioniser. This is advantageous as the gas-phase charge states of the ions generated by such an ion source are particularly well correlated to the charge states that the analytes have when in solution. As the charge states in solution are correlated to the elution time from the electrophoretic mobility separator, this enables the gas-phase analyte ions to be provided in a manner such that they are at least somewhat temporally separated according to their gas-phase charge states.

A solution of analytes is preferably flowed through a capillary in the separator and a potential difference may be applied across the capillary such that the analytes separate according to their electrophoretic mobility. The direction of flow of the analyte solution within the separator may be the same as the direction in which the ions are urged by the electric field, or may be different. Ions may elute from the electrophoretic mobility separator in order of high to low electrophoretic mobility or in order of low to high electrophoretic mobility.

The flow rate of the analyte solution may be varied with time in order to determine the rate at which the different analytes elute.

The spectrometer may comprise combinations of one of more of the above described devices, and ions may be transmitted between the devices. The operation of each of the devices may be varied as a function of the elution time from the electrophoretic mobility separator in the manner described above.

As described above, although there is a weaker correlation between mass to charge ratio, charge state and retention time for other liquid chromatography techniques, some correlation does exist. Accordingly, from a fourth aspect the present invention provides a method of mass spectrometry or ion mobility spectrometry comprising:

separating analytes in a liquid chromatography separator such that different analytes elute from the separator at different times;

ionising the separated analytes after they have eluted from the separator so as to form analyte ions that are separated from each other;

transmitting the analyte ions to at least one device that manipulates the ions; and varying the operation of the at least one device based on the elution time of the analyte ions from the separator.

The method according to the fourth aspect may have any one or combination of features described in relation to the third aspect of the invention, except wherein the electrophoretic mobility separation is replaced by liquid chromatography separation.

The liquid chromatography may separate the analytes in a based on their charge in solution or based on their masses.

The liquid chromatography may be Size Exclusion Chromatography ("SEC"), Ion Exchange Chromatography ("IEX") or pH gradient chromatography.

Preferably, the separation is mass, charge or mass to charge ratio dependent. For example, Size Exclusion Chromatography separates analytes by hydrodynamic radius which, as with electrophoretic mobility, is strongly correlated to mass. There is however no correlation to mass to charge ratio as the separation is not dependent on the charge of the analytes in solution.

The separation may be dependent on the charge in solution of the analytes. For example, Ion exchange chromatography is strongly solution charge dependent.

The present invention also provides a mass spectrometer or ion mobility spectrometer arranged and configured to perform any one of the methods described herein.

From the first aspect, the present invention provides a mass spectrometer or ion mobility spectrometer comprising:

a separator for separating analytes according to their electrophoretic mobilities;

an ion source for ionising the separated analytes; a mass filter;

storage means for storing a predetermined relationship between elution times of the analytes from the separator, mass to charge ratios of the analyte ions, and charge states of the analyte ions; and a controller arranged and configured to control the spectrometer to:

separate analytes in said separator such that analytes having different electrophoretic mobilities elute from the separator at different times;

ionise the separated analytes in the ion source as they elute from the separator so as to form analyte ions that are separated from each other;

filter the separated analyte ions according to their mass to charge ratio in the mass filter; and vary the mass to charge ratios of the ions transmitted by the mass filter as a function of the elution time of the analytes from the separator and according to said predetermined relationship such that substantially only ions having one or more desired charge states are transmitted by the mass filter.

The mass spectrometer may be arranged and configured to perform any one or combination of the optional or preferred methods described in relation to the first aspect of the present invention.

From the second aspect, the present invention provides a mass spectrometer or ion mobility spectrometer comprising:

an electrophoretic mobility separator or a liquid chromatography separator for separating analytes;

an ion source for ionising the separated analytes;

a filter for filtering analyte ions according to a physicochemical property;

storage means for storing a predetermined relationship between elution times of the analytes from the separator, the physicochemical property values of the analyte ions, and charge states of the analyte ions; and a controller arranged and configured to control the spectrometer to:

separate analytes in said electrophoretic mobility separator or said liquid chromatography separator such that analytes elute from the separator at different times;

ionise the separated analytes in the ion source as they elute from the separator so as to form analyte ions that are separated from each other;

filter the separated analyte ions according to said physicochemical property in the filter; and vary the physicochemical property values of the ions transmitted by the filter as a function of the elution time of the analytes from the separator and according to said predetermined relationship such that substantially only ions having one or more desired charge states are transmitted by the filter.

The mass spectrometer may be arranged and configured to perform any one or combination of the optional or preferred methods described in relation to the second aspect of the present invention.

From the third aspect the present invention provides a mass spectrometer or ion mobility spectrometer comprising:

a separator for separating analytes such that analytes having different electrophoretic mobilities elute from the separator at different times;

an ion source for ionising the separated analytes after they have eluted from the separator so as to form analyte ions that are separated from each other;

at least one device for receiving and manipulating the analyte ions; and means for varying the operation of the at least one device based on the elution time of the analyte ions from the separator.

The mass spectrometer may be arranged and configured to perform any one or combination of the optional or preferred methods described in relation to the third aspect of the present invention.

From the fourth aspect the present invention provides a mass spectrometer or ion mobility spectrometer comprising:

a liquid chromatography separator for separating analytes such that different analytes elute from the separator at different times;

an ion source for ionising the separated analytes after they have eluted from the separator so as to form analyte ions that are separated from each other;

at least one device for receiving and manipulating the analyte ions; and means for varying the operation of the at least one device based on the elution time of the analyte ions from the separator.

The mass spectrometer may be arranged and configured to perform any one or combination of the optional or preferred methods described in relation to the fourth aspect of the present invention.

The spectrometer may comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The spectrometer may comprise an electrostatic ion trap or mass analyser that employs inductive detection and time domain signal processing that converts time domain signals to mass to charge ratio domain signals or spectra. Said signal processing may include, but is not limited to, Fourier Transform, probabilistic analysis, filter diagonalisation, forward fitting or least squares fitting.

The spectrometer may comprise:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprise a device arranged and adapted to supply an AC or RF voltage to the electrodes. The AC or RF voltage preferably has an amplitude selected from the group consisting of: (i)<50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i)<100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv)>10.0 MHz.

The spectrometer may comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide is preferably maintained at a pressure selected from the group consisting of: (i)<0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix)>1000 mbar.

Analyte ions may be subjected to Electron Transfer Dissociation ("ETD") fragmentation in an Electron Transfer Dissociation fragmentation device. Analyte ions are preferably caused to interact with ETD reagent ions within an ion guide or fragmentation device.

In order to effect Electron Transfer Dissociation optionally either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions preferably comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2'dipyridyl; (xiii) 2,2'biquinoline; (xiv) 9-anthracenecarbonitrile; (xv) dibenzothiophene; (xvi) 1,10'-phenanthroline; (xvii) 9'anthracenecarbonitrile; and (xviii) anthraquinone; and/or (c) the reagent ions or negatively charged ions comprise azobenzene anions or azobenzene radical anions.

According to a particularly preferred embodiment the process of Electron Transfer Dissociation fragmentation comprises interacting analyte ions with reagent ions, wherein the reagent ions comprise dicyanobenzene, 4-nitrotoluene or azulene reagent ions.

According to the preferred embodiment the operating parameters of a mass spectrometer are altered during the capillary electrophoresis elution in such a way that the known or observed correlation between capillary electrophoresis elution time, charge state and mass to charge ratio value is utilised to optimise the performance of the mass spectrometer throughout the experiment.

One or more functional parameters of the downstream device may be changed or scanned during the period of separation and synchronised to the period of separation so as to enhance or simplify the final ion data recorded.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENT

Capillary electrophoresis ("CE") is a known technique which is used to separate ionic species in a conductive medium in the presence of an electric field. Capillary electrophoresis causes ions in solution to migrate with velocities based on their solution charge (i.e. charge when in solution), hydrodynamic radius and frictional forces.

The velocity of an ion under conditions of capillary electrophoresis separation is given by:

$$v_a = E \cdot \mu \quad (1)$$

wherein $\mu$ is the electrophoretic mobility, $v_a$ is the velocity of the analyte and E is the electric field strength.

The electrophoretic mobility of an analyte depends on the viscosity of the medium, the size and shape of the analyte, and the solution charge. For peptides, the electrophoretic mobility can be related to the size of the peptide and may be estimated from its molecular weight. The Offord model (as detailed in: "Electrophoretic Mobilities of Peptides on Paper and their Use in the Determination of Amide Groups", R. E. Offord, Nature 211, 591-593, 6 Aug. 1966) estimates the electrophoretic mobility $\mu$ as:

$$\mu \propto \frac{q}{MW^{2/3}} \quad (2)$$

wherein μ is the electrophoretic mobility and MW is the molecular weight of the analyte. When coupling a capillary electrophoresis device to a mass spectrometer, the correlation between mass to charge ratio value, charge state and capillary electrophoresis retention time can be clearly demonstrated. An example of a capillary electrophoresis device coupled to a mass spectrometer is described in "Utility of CE-MS Data in Protein Identification", Brad J. Williams, William K. Russell, and David H. Russell, Anal. Chem. 2007, 79, 3850-3855. An arrangement is disclosed wherein capillary electrophoresis separation is followed by Matrix Assisted Laser Desorption Ionisation ("MALDI"). MALDI ionisations almost exclusively yield singly charged ions. Clear trends in the mass to charge ratio versus retention time are shown. These correlations follow trends in the capillary electrophoresis separation related to the solution charge state and size (correlated to the molecular weight) of the analytes.

Electrospray ionization ("ESI") ion sources may be coupled to a mass spectrometer in order to ionise polar compounds such as peptides. The electrospray ionisation of peptides may result in ions with several different charge states. There is a strong correlation between the charge state in solution and the dominant charge state produced by the electrospray process. For peptides, the charge in solution and the charge state in the gas phase are both strongly related to the number of basic residues on the peptide. In particular, ions which are singly or doubly charged in solution appear predominantly as these charge states in the gas phase. Ions of higher charge state in solution may exist in more than one charge state in the gas phase. The observed correlation between solution phase and gas phase charge state and the strong correlation between molecular weight and solution phase hydrodynamic radius results in a capillary electrophoresis elution order correlated to both charge state and mass to charge ratio value observed in the electrospray mass spectrum of peptides.

Separation in capillary electrophoresis also depends on the electroosmotic flow of the buffer solution. The direction of the electroosmotic flow with relation to the direction of electrophoretic migration of the analyte ions is governed by the composition or coating applied to the walls of the capillary electrophoresis capillary. Electroosmotic flow can be used to govern the elution order of analytes. For example, if the electroosmotic flow is opposed to the electrophoretic migration then analytes with low mobility will elute before analytes with higher electrophoretic mobility.

Figure 1:
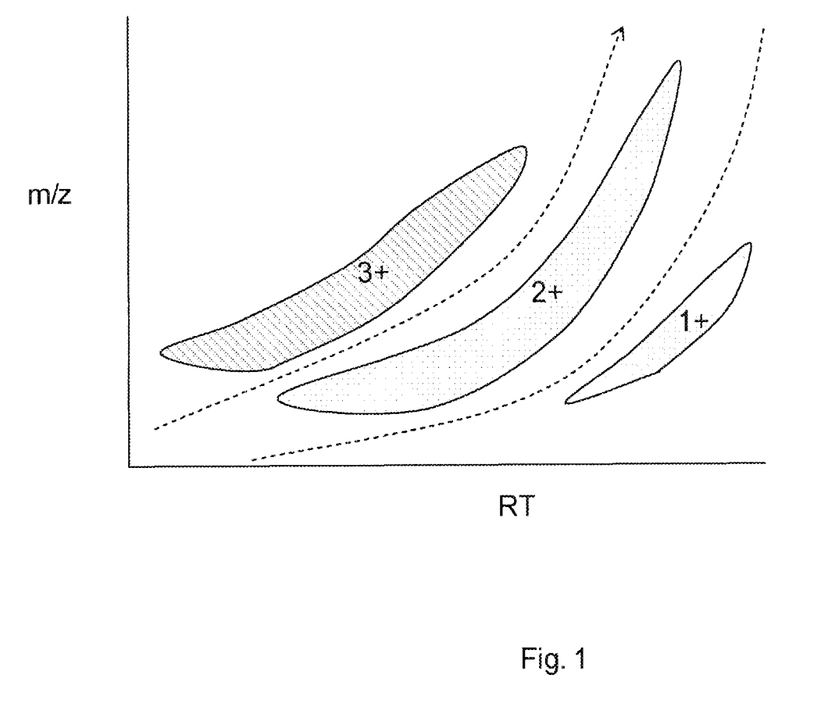
FIG. 1 shows a plot of mass to charge ratio value versus capillary electrophoresis retention time for a mixture of peptides ionised by electrospray, wherein the ions elute in order of high to low electrophoretic mobility.

A preferred embodiment of the present invention will now be described with reference to FIG. 1. According to the preferred embodiment, a mixture of peptides is subjected to capillary electrophoresis and the peptides are then ionised by an electrospray ioniser. The resulting ions are then mass analysed in a mass spectrometer so as to determine their mass to charge ratios. FIG. 1 shows a plot of the mass to charge ratios of the ions as a function of their capillary electrophoresis retention time. It can be observed that the analyte ions are separated into three enclosed areas that represent singly (1+), doubly (2+) and triply (3+) charged gas-phase ions. In this example, ions elute in order of high to low electrophoretic mobility. The ions which elute first are ions with the highest solution charge state and lowest mass to charge ratio.

Figure 2:
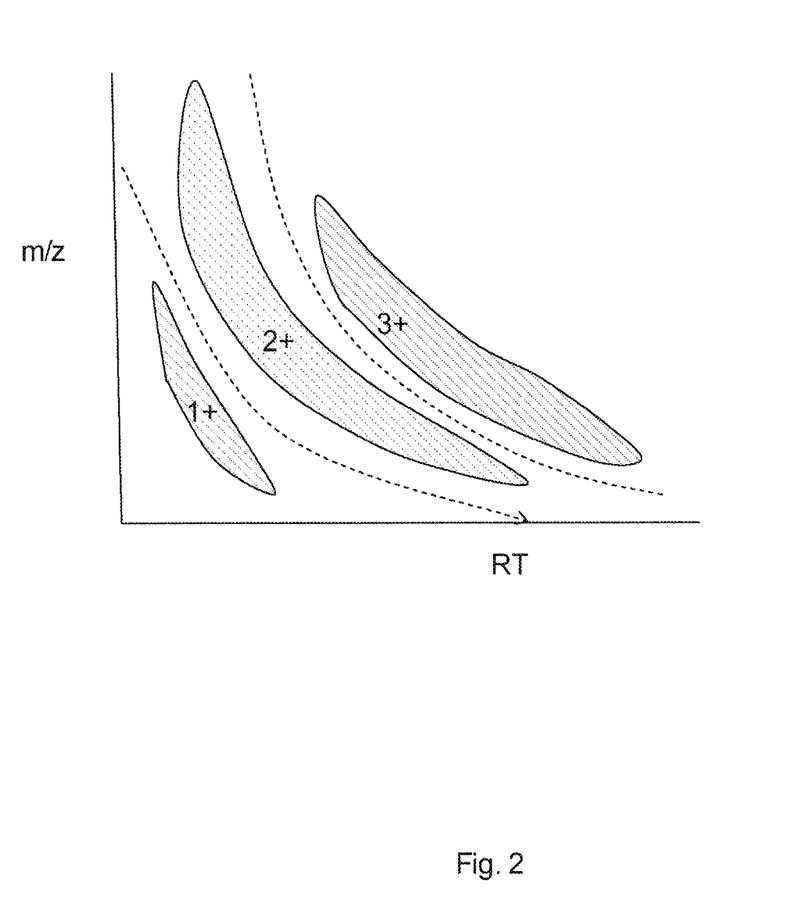
FIG. 2 shows a similar plot to FIG. 1, except wherein the ions elute in order of low to high electrophoretic mobility.

FIG. 2 shows a plot corresponding to that in FIG. 1, except wherein the ions elute in order of low to high electrophoretic mobility. The order of elution is reversed by reversing the electroosmotic flow.

It will be observed that in the embodiments of both FIGS. 1 and 2 there is correlation between elution time and mass to charge ratio within each band. The analytes having different gas phase charge states are separated from each other.

Figure 3:
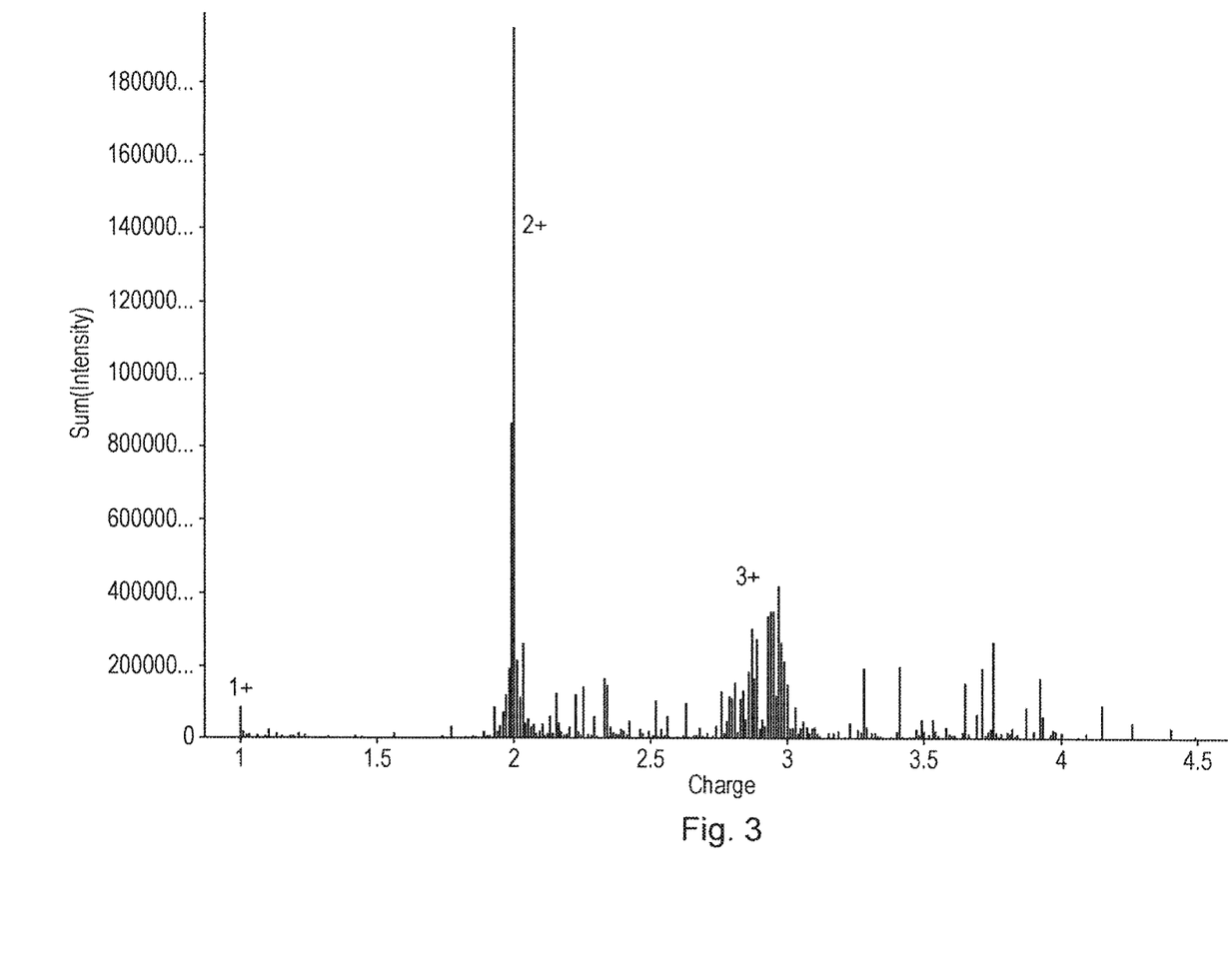
FIG. 3 shows a plot of intensity versus the average charge state of peptides separated by nano-flow UPLC and ionized by positive ion electrospray.

FIG. 3 shows a plot of intensity versus the average charge state for peptides from a tryptic digest of a mixture of four proteins separated by nano-flow high pressure liquid chromatography and which have been ionised by positive ion electrospray. The average charge state is an intensity weighted value of the charge states of the mass spectral peaks associated with each peptide. It is clear that most of the ions formed cluster around and close to an average charge state of 2+ or 3+, representing doubly charged and triply charged ions. This demonstrates that the electrospray process generates predominantly a single charge state for a given peptide. This is most clearly seen for the doubly charged ions, which are shown by peaks distributed closely and fairly evenly about the 2+ charge state. However, the peaks are less evenly distributed about the 3+ charge state and FIG. 3 shows that many peaks are distributed just below the 3+ value. This indicates that some of the peptides that form triply charged ions also form doubly charged ions. The dominant charge states produced by electrospray ionisation correlate with the charge states in solution that have been separated by the capillary electrophoresis.

Referring again to FIG. 1 or 2, at a given time during capillary electrophoresis separation, doubly charged ions (2+) will form within a distinct range of mass to charge ratios that lies between the upper and lower dashed lines. Very little, if any, signal from peptides of lower or higher gas phase charge states will be present within this range. In FIG. 1, the mass to charge ratios of the ions that have a charge state of 2+ increase as the capillary electrophoresis retention time increases. Conversely, in FIG. 2 the mass to charge ratios of the ions that have a charge state of 2+ decrease as the capillary electrophoresis retention time increases.

According to a preferred embodiment a mass filter, such as a quadrupole mass filter, may be located downstream of a capillary electrophoresis separation device and an ion source. The mass filter is preferably located upstream of another mass analyser, such as a Time of Flight mass spectrometer. In operation, the mass filter may be operated in a bandpass mode such that only ions having mass to charge ratios within the ranges bounded by the dotted lines in FIG. 1 or 2 are transmitted. The scan law of the quadrupole mass filter is preferably synchronised with the capillary electrophoresis elution time. In this way, the final mass spectrum may be enriched with ions of particular charge states.

Figure 4:
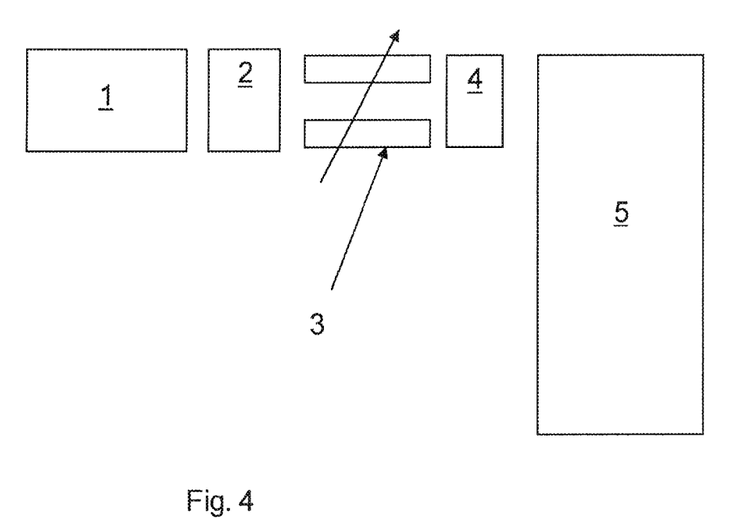
FIG. 4 shows an apparatus illustrating an embodiment of the invention.

FIG. 4 shows a mass spectrometer according to an embodiment of the present invention. Analytes are preferably first separated in solution by a capillary electrophoresis device 1. The analytes are then ionised by an ion source 2. The ion source 2 preferably comprises an Atmospheric Pressure Ionization ("API") ion source. An analytical filter 3 such as a quadrupole mass filter 3 is preferably provided downstream of the ion source 2 and is preferably scanned or stepped continuously or discontinuously in synchronisation with the capillary electrophoresis device 1 such that only ions having a combination of mass to charge ratios within a desired range and a capillary electrophoresis retention time within a desired range are transmitted at any instant in time. The ions transmitted may be passed directly to a Time of Flight mass analyser 5 or may be caused to dissociate into product ion species in a fragmentation device 4.

Figure 5:
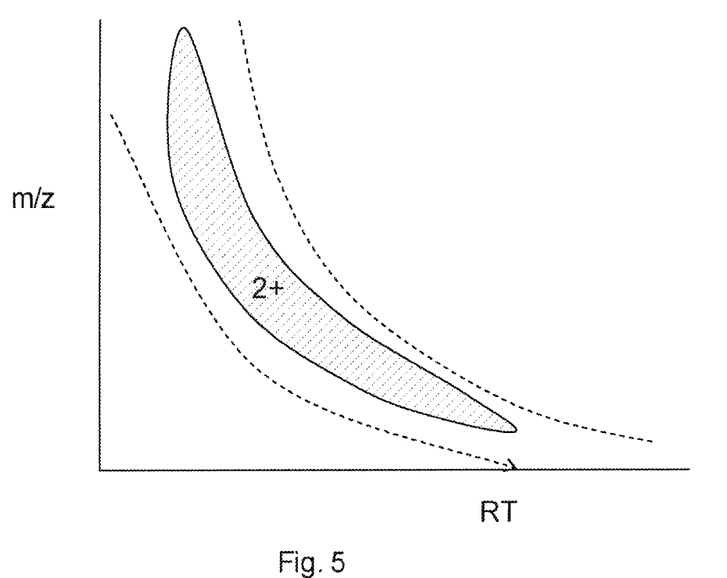
FIG. 5 shows a mass to charge ratio versus capillary electrophoresis retention time plot similar to FIG. 2, except after allowing only the doubly charged ions to be transmitted.

FIG. 5 shows a plot of mass to charge ratio versus capillary electrophoresis retention time that is similar to that of FIG. 2, except that the ions have been filtered after separation in the capillary electrophoresis device 1 such that only the doubly charged ions (2+) have been transmitted by the filter 3.

Figure 6:
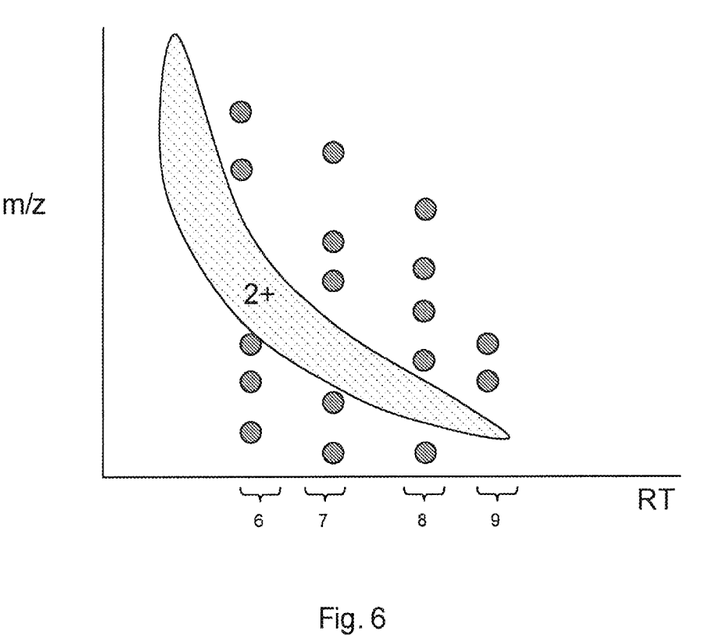
FIG. 6 shows the mass to charge ratio versus capillary electrophoresis retention time plot as described in FIG. 5 after fragmenting the transmitted ions.

FIG. 6 shows a plot of mass to charge ratio versus capillary electrophoresis retention time for the ions of FIG. 5 after they have been fragmented in fragmentation device 4. The properties of the resulting fragment ions are illustrated as the circles located in capillary electrophoresis retention time regions 6, 7, 8, 9. The retention times associated with the fragment ions represent the retention times of their respective parent ions, as the fragment ions have been generated after the parent ions have been separated by capillary electrophoresis and the fragment ions themselves have not been subjected to separation by capillary electrophoresis. Filtering the doubly charged ions prior to fragmentation provides the advantage that the likelihood of the fragment ion intensity or mass to charge ratio information being corrupted due to mass interference is reduced.

According to an alternative embodiment the filter 3 may alternatively be used as a high-pass or low-pass mass to charge ratio filter, rather than a band-pass filter, in order to only transmit ions above or below a desired mass to charge ratio for a given retention time. For example, the filter 3 could be varied with retention time so as to only transmit ions above the upper dashed line in FIG. 1 or FIG. 2. In this manner, only ions having a gas phase charge state of 3+ would be transmitted for subsequent analysis or fragmentation etc. Similarly, the filter 3 could be varied with retention time so as to only transmit ions below the lower dashed line in FIG. 1 or FIG. 2 such that only ions having a gas phase charge state of 1+ would be transmitted for subsequent analysis or fragmentation etc. Alternatively, more than one mass to charge ratio transmission window may be scanned or set simultaneously. This may be achieved, for example, by applying a broadband resonance excitation waveform with frequency notches (i.e. with specific frequencies omitted) to a quadrupole mass filter. In this way, multiple mass to charge ratio regions may be transmitted simultaneously that track several mass to charge ratio trend lines in the capillary electrophoresis elution profile. For example, the ions having a gas phase charge state of 1+ and 3+ in FIG. 1 or 2 might be transmitted simultaneously and the ions of charge state 2+ might be filtered out.

Although the embodiments described above relate to a quadrupole mass filter that is scan linked with capillary electrophoresis separation, another type of filter may be used to achieve similar results. For example, a differential ion mobility filter or Field Asymmetric Ion Mobility Spectrometry filter (FAIMS) may be arranged to scan synchronously with the capillary electrophoresis elution. Alternatively, an ion mobility separator (IMS) filter such as a Differential Mobility Analyser ("DMA") may be used. Both of these devices separate ions based on gas phase ion mobility. These devices may be operated at atmospheric pressure or at sub-atmospheric pressure.

In a second embodiment of the present invention the strong correlation between capillary electrophoresis elution time and mass to charge ratio for a given charge state may be used to optimise the operation of a downstream gas phase ion mobility separator (IMS). This may be a linear DC field drift cell or a travelling wave IMS device. In this mode, a nested capillary electrophoresis IMS acquisition may be performed producing a comprehensive CE-IMS two dimensional separation. At any instance in time only a narrow mass to charge ratio range or electrophoretic mobility range for a given charge state will be delivered to the IMS device. Based upon this knowledge, multiple packets of ions may be released into the IMS device sequentially while ions are being separated in the IMS device. The frequency and/or duty cycle at which these packets of ions are released into the gas phase IMS device may be arranged such that no overlapping of ion species occurs. This mode of operation is advantageous to minimize space-charge effects such as peak broadening or drift time shifting in the gas phase IMS device.

One or more travelling wave may be conveyed along the IMS device as ions pass through the device, e.g. in order to drive ions through the IMS device. The travelling wave is preferably a DC potential hill or well that is conveyed along the device. The amplitude and/or velocity and/or DC field strength of the travelling wave may be varied so as to optimise the IMS conditions (e.g. resolution or elution time) for the range of mass to charge ratio values or solution phase mobility eluting from the capillary electrophoresis device. Additionally, or alternatively, other IMS conditions could be varied as a function of the elution time from the capillary electrophoresis device.

In another embodiment, a fragmentation device is provided downstream of the capillary electrophoresis device. The conditions of the fragmentation device may be changed during the capillary electrophoresis elution time in order to optimise the conditions for efficient fragmentation of ions eluting from the capillary electrophoresis device. This may comprise, for example, varying the collision energy for collisionally induced dissociation (CID) or varying the reaction time for electron transfer dissociation (ETD) or electron capture dissociation (ECD) in the fragmentation device.

Alternatively, the fragmentation technique may be varied as a function of elution time from the capillary electrophoresis device. For example, in the example shown in FIG. 1 multiply charged ions elute first from the capillary electrophoresis device and singly charged ions elute at later retention times. Different fragmentation techniques may be preferred for ions of different charge states. In this case, it may be advantageous to utilise a technique such as ETD at the start of the capillary electrophoresis separation in order to efficiently fragment ions of high charge state. However, ions of lower charge state elute from the capillary electrophoresis device at later retention times and it may therefore be desirable to switch to CID fragmentation.

Many other fragmentation methods exist which require different conditions for differing mass to charge ratio values or charge states which will benefit from this approach.

In another embodiment the performance of an orthogonal acceleration Time of Flight mass analyser may be optimized using the correlation between mass to charge ratio and capillary electrophoresis elution time. For example, a relatively narrow mass to charge ratio range eluting from a capillary electrophoresis device at a given time may be released to the Time of Flight orthogonal sampling region as a pulse. The orthogonal acceleration voltage pulse may be synchronised to the release of this pulse such that this mass to charge ratio range in transmitted into the Time of Flight analyser with high efficiency. As the capillary electrophoresis separation proceeds the mass to charge ratio range eluting from the device changes and hence the time delay between release of an ion pulse and the energising of the orthogonal acceleration pulse may be changed so as to maintain the highest sampling efficiency. As such, for a given charge state over the entire mass to charge ratio range, high sampling efficiency may be maintained.

In another embodiment a mass selective ion trap may be arranged downstream of the capillary electrophoresis device. The performance of the mass selective ion trap may be improved by changing the mass range over which the analytical ion trap scans to accommodate the mass to charge ratio range eluting from the capillary electrophoresis device. In this way, the speed of mass selective ejection (i.e. amu per unit time) may be minimised, thus maximising mass resolution.

Combinations of the above embodiments may be employed in order to optimise multiple performance attributes of multiple different downstream devices.

Although the present invention has been described with reference to preferred embodiments, it will be understood by those skilled in the art that various changes in form and detail may be made without departing from the scope of the invention as set forth in the accompanying claims.

For example, separation techniques other than the capillary electrophoresis described may be used. Separation techniques which use solution phase electrophoretic mobility may be used such as, for example, Capillary Electrochromatography ("CEC") or Micellar Electrokinetic Chromatography ("MEKC"). Alternatively, Size Exclusion Chromatography ("SEC") may be used, which separates analytes based on size and also produces separations with a strong indicator weight dependence. As the separation has a molecular weight correlation, this separation may also be linked with optimisation of downstream devices in the mass spectrometer.

Although there is far weaker correlation between mass to charge ratio, charge state and retention time for other liquid chromatography techniques, some correlation does exist and similar linked experiments using other liquid chromatography techniques to optimise performance can be envisaged. For example pH gradient chromatography or ion exchange chromatography etc may be used.

The techniques described can be applied to comprehensive two dimensional (2D) chromatography. For example, with normal phase liquid chromatography (LC) as the first dimension and rapid profiling of the LC peaks with fast capillary electrophoresis separation in the second dimension. With the correlated mass to charge ratio and or charge state output of the capillary electrophoresis used to optimize the conditions of the downstream devices.

The invention claimed is:

1. A method of mass spectrometry or ion mobility spectrometry comprising:
   separating analytes in a separator such that analytes having different electrophoretic mobilities elute from the separator at different times;
   ionising the separated analytes as they elute from the separator so as to form analyte ions that are separated from each other;
   transmitting the separated analyte ions to a mass filter;
   obtaining a predetermined relationship between the elution times of the analytes from the separator, the mass to charge ratios of the analyte ions, and the charge states of the analyte ions;
   selecting one or more charge states of the analyte ions desired to be transmitted by the mass filter; and
   varying the mass to charge ratios of the ions transmitted by the mass filter as a function of the elution time of the analytes from the separator and according to said predetermined relationship such that substantially only ions having said one or more desired charge states are transmitted by the mass filter.

2. The method of claim 1, wherein said predetermined relationship is known or determined in advance of said step of varying the mass to charge ratios of the ions transmitted by the mass filter.

3. The method of claim 1, wherein for analyte ions in each of said one or more desired charge states in said predetermined relationship, the mass to charge ratios progressively increase without decreasing, or progressively decrease without increasing, as a function of increasing electrophoretic mobility; and/or
   wherein the mass to charge ratio or range of mass to charge ratios transmitted by the mass filter at any given time progressively increases without decreasing, or progressively decreases without increasing, as a function of increasing electrophoretic mobility such that said one or more desired charge states are transmitted by the mass filter.

4. The method of claim 3, wherein the mass to charge ratio or range of mass to charge ratios transmitted by the mass filter continuously increases or continually decreases, or increases or decreases in a stepped manner.

5. The method of claim 1, wherein the analyte ions in each of said one or more desired charge states in said predetermined relationship follow a trend of mass to charge ratio as a function of electrophoretic mobility, and wherein the filter is varied so as to transmit analyte ions that follow said trend.

6. The method of claim 1, comprising separating the analytes so that they elute from the separator over a period of time and varying the mass to charge ratios of the ions transmitted by the filter in synchronism with said period of time.

7. The method of claim 1, comprising transmitting the analyte ions of said one or more desired charge states from said filter to a fragmentation or reaction region; fragmenting the analyte ions to form fragment ions, or reacting the analyte ions with other ions or molecules to form product ions; and mass analysing or ion mobility analysing the fragment or product ions.

8. A method of mass spectrometry or ion mobility spectrometry comprising:
   separating analytes in an electrophoretic mobility separator or in a liquid chromatography separator such that different analytes elute from the separator at different times;
   ionising the separated analytes after they elute from the separator so as to form analyte ions that are separated from each other;
   transmitting the separated analyte ions to a filter for filtering ions according to a physicochemical property;
   obtaining a predetermined relationship between the elution times of the analytes from the separator, the physicochemical property values of the analyte ions, and the charge states of the analyte ions;
   selecting one or more charge states of the analyte ions desired to be transmitted by the filter; and
   varying the physicochemical property values of the ions transmitted by the filter as a function of the elution time of the analytes from the separator and according to said predetermined relationship such that substantially only ions having said one or more desired charge states are transmitted by the mass filter.

9. The method of claim 8, wherein said physicochemical property is ion mobility in a Field Asymmetric Ion Mobility Spectrometer (FAIMS) device.

10. A mass spectrometer or ion mobility spectrometer arranged and configured to perform the method of claim 1.

* * * * *